United States Patent
Nakamura

(10) Patent No.: US 7,328,606 B2
(45) Date of Patent: Feb. 12, 2008

(54) EXHAUST GAS MEASURING DEVICE AND METHOD FOR MEASURING EXHAUST GAS

(75) Inventor: Hiroshi Nakamura, Kyoto (JP)

(73) Assignee: Horiba, Ltd., Kyoto (JP)

( * ) Notice: Subject to any disclaimer, the term of this patent is extended or adjusted under 35 U.S.C. 154(b) by 0 days.

(21) Appl. No.: 11/278,605

(22) Filed: Apr. 4, 2006

(65) Prior Publication Data

US 2006/0218988 A1   Oct. 5, 2006

(30) Foreign Application Priority Data

Apr. 4, 2005   (JP) ............................. 2005-107191

(51) Int. Cl.
*G01M 15/00*   (2006.01)
(52) U.S. Cl. .................... 73/118.1; 73/23.31
(58) Field of Classification Search ................ 73/118.1, 73/23.31, 23.32, 116, 117.2, 117.3
See application file for complete search history.

(56) References Cited

U.S. PATENT DOCUMENTS

| | | | |
|---|---|---|---|
| 5,599,179 A | 2/1997 | Lindner et al. | |
| 6,470,732 B1 * | 10/2002 | Breton | 73/23.31 |
| 6,912,480 B2 * | 6/2005 | Black | 702/183 |
| 2004/0064243 A1 * | 4/2004 | Nakamura | 701/114 |

FOREIGN PATENT DOCUMENTS

| | | |
|---|---|---|
| EP | 1127730 | 8/2001 |
| EP | 1405989 | 4/2004 |
| EP | 1450139 | 8/2004 |
| JP | 08-128948 | 5/1996 |

OTHER PUBLICATIONS

Docquier N et al., "Combustion Control And Sensors: A Review", Progress In Energy And Combustion Science, Elsevier Science Publishers, vol. 28, No. 2, 2002, pp. 107-150, Amsterdam, NL.

* cited by examiner

*Primary Examiner*—Eric S. McCall
(74) *Attorney, Agent, or Firm*—Brooks Kushman P.C.

(57) ABSTRACT

With the exhaust gas measuring device and the exhaust gas measuring method, the workload of the internal combustion engine is calculated based on a discharged amount of a component related to a carbon compound such as CO, $CO_2$ and THC in the exhaust gas discharged from the internal combustion engine. As a result, the workload of the internal combustion engine can be calculated easily without using torque data of the ECU and the mass of each component in the exhaust gas discharged from the internal combustion engine per unit workload can be calculated.

9 Claims, 4 Drawing Sheets

EXHAUST GAS MEASURING DEVICE AND METHOD FOR MEASURING EXHAUST GAS

BACKGROUND OF THE INVENTION

1. Field of the Invention

This invention relates to an exhaust gas measuring device that measures exhaust gas discharged from an internal combustion engine of a vehicle and a method for measuring exhaust gas, and more specifically, to an exhaust gas measuring device and a method for measuring exhaust gas that makes it possible to obtain a workload of the internal combustion engine and an amount of exhaust gas per the workload.

2. Background Art

An exhaust gas measuring device that measures the concentration of a predetermined component such as CO, $CO_2$ or $NO_x$ contained in the exhaust gas discharged from an internal combustion engine (an engine) provided for a vehicle and that analyzes the exhaust gas is known. (For example, Japan Patent Laid-open No. 8-128948.)

A main object of the exhaust gas measuring device is not only to know the concentration of a predetermined component contained in the exhaust gas but also to know the emission mass of the exhaust gas or mass of the predetermined component contained in the exhaust gas in order to measure what influence is exerted on atmospheric contamination by the exhaust gas discharged from the internal combustion engine.

An index calculated by converting the mass of the exhaust gas discharged from the internal combustion engine or the mass of the predetermined component contained in the exhaust gas into an amount per unit workload (unit output) of the internal combustion engine, namely the mass of the exhaust gas discharged from the internal combustion engine per unit output is used for performance assessment or legal restrictions of the internal combustion engine.

The index is used in a case that measurement is conducted for a stand-alone internal combustion engine such as an internal combustion engine of an especially large-size vehicle that does not have a large-size chassis dynamo meter accepted by the large-size vehicle.

Since the workload (output) of the internal combustion engine is expressed by a product of torque and a rotation number, the torque and the rotation number of the internal combustion engine have to be obtained directly in order to calculate the workload. However, it is not easy to obtain either of the torque and the rotation number, and there has almost never been an exhaust gas measuring device that is provided with a sensor to obtain the torque especially.

Then in order to obtain the workload of the internal combustion engine, conventionally there was a method to use torque data obtained by the use of an ECU by calculating the fuel injection amount injecting to a fuel engine or a method to detect torque by the use of a torque sensor actually mounted on a shaft of an internal combustion engine.

However, since the torque data obtained by the ECU is based on a fuel supplying amount near an internal combustion engine or an inhaled air amount, there exists a time-lag between the torque data and the data of the amount of the exhaust gas discharged from an exhaust duct (a tail pipe) arranged separated from the internal combustion engine. As a result, the contemporary discharged amount of the exhaust gas of the internal combustion engine per workload can not always be calculated. In addition, there is a problem that a torque sensor is extremely difficult to mount. Furthermore, there might be a case that a vehicle is not provided with an interface such as an ECU signal or an OBD to output the torque data to outside of the vehicle. In addition, even though the interface is provided, a signal mode may vary for each vehicle and is difficult to obtain. It is a situation that the workload of the internal combustion engine can not be measured accurately and easily.

SUMMARY OF THE INVENTION

It is an object of the present claimed invention to provide an exhaust gas measuring device and an exhaust gas measuring method that make it possible to measure the workload (output) of the internal combustion engine on a real time basis and mass of the exhaust gas per unit workload calculated from the measured workload without using torque data obtained from the ECU nor a torque sensor and to conduct measurement not only for an internal combustion engine alone but also for a large-size car while actually running.

More specifically, the exhaust gas measuring device and the exhaust gas measuring method in accordance with the present claimed invention are characterized by calculating the workload of the internal combustion engine based on the discharged amount of the component related to the carbon compound in the exhaust gas discharged from the internal combustion engine.

In accordance with this arrangement, since it is possible to obtain the workload of the internal combustion engine only from an amount of the component related to the carbon compound measured by the exhaust gas measuring device, it is possible to calculate the workload of the internal combustion engine easily by the use of the exhaust gas measuring device alone without using the torque data of the ECU and to obtain the workload of the internal combustion engine in spite of a case that the internal combustion engine of a large-size car to which a chassis dynamo can not be used.

Since the discharged amount of the exhaust gas can be obtained easily by a flow meter, it is possible to easily calculate an index calculated by converting the discharged amount of the exhaust gas into the unit workload (the unit output) of the internal combustion engine, namely the discharged mass of the exhaust gas per unit output.

In addition, since both the workload of the internal combustion engine and the discharged mass of the exhaust gas (and each component) are measured from the exhaust gas, time-lag generated between them is zero in principle. As a result, a complicated synchronous mechanism that is required for a case of using the torque data obtained from the ECU or the torque sensor becomes unnecessary, and it becomes possible to conduct a continuous measurement in a time-series order on a real time basis.

Furthermore, since the exhaust gas measuring device can be loaded on a vehicle, the exhaust gas can be measured for a large-size car while the car is in motion, which used to be impossible. In addition, since the exhaust gas of different vehicles can be measured by the use of the same measuring device, it is possible to conduct a measurement of high reliability that objectively shows a difference for each vehicle.

In order to measure an amount of a component related to the carbon compound in the exhaust gas discharged from the internal combustion engine easily by the use of a conventional analyzer, it is preferable that the exhaust gas concentration measuring part that measures the concentration of the component related to the carbon compound in the exhaust gas discharged from the internal combustion engine is provided and the discharged amount of the component related to the carbon compound is calculated from the measured concentration of the component related to the carbon compound and the flow rate of the exhaust gas.

As mentioned above, the mass of the exhaust gas discharged from the internal combustion engine per unit workload or the mass of a predetermined component in the exhaust gas discharged from the internal combustion engine per unit workload may be calculated based on the workload of the internal combustion engine.

As a concrete embodiment, it is preferable that the component related to the carbon compound to be measured is at least CO, $CO_2$ and a hydrocarbon class. This is because almost all the carbon compound generated due to combustion of the fuel of the internal combustion engine consists of above-mentioned CO, $CO_2$ and a hydrocarbon class. Since a ratio of $CO_2$ is high among them, $CO_2$ alone may be an object component to be measured depending on an intended purpose such that high accuracy is not required.

As concrete steps to calculate the workload of the internal combustion engine conceived is that an amount of fuel consumption is calculated by the use of a carbon balance method from the discharged amount of the component related to the carbon compound and the workload of the internal combustion engine is calculated by multiplying the combustion energy of the predetermined fuel by the combustion efficiency of the internal combustion engine.

If the concentration of the component related to the carbon compound in the exhaust gas is obtained by integration in a particular time zone and a discharged amount of the component related to the carbon compound in the exhaust gas discharged from the internal combustion engine in the time zone is calculated based on the integrated value of the concentration, it is possible to obtain the average mass of each component in the exhaust gas discharged per unit workload in the time zone. In addition, if the time zone is set short, the mass of each component in the exhaust gas discharged from the internal combustion engine per unit workload can be obtained on a real time basis.

It is preferable that the time zone is determined in accordance with a pulsation cycle of flow of the exhaust gas. For example, the time zone may be set to correspond to a period from a starting time to an ending time of one stroke of a piston cylinder equivalent to one rotation in the internal combustion engine or the severalfold period and the measurement may be continuously conducted with the time zone set as one unit of the measurement. Since it is possible for the exhaust gas measuring device to obtain the mass of each component in the exhaust gas discharged for one driving cycle of the piston cylinder of the internal combustion engine (every pulsation of the internal combustion engine) and its workload respectively, the exhaust gas measuring device is suitable for a case that the performance or characteristics of the internal combustion engine is required to be checked for details.

It is preferable that the exhaust gas measuring device in accordance with this invention obtains the mass discharged per unit workload concerning various components that are contained in the exhaust gas discharged from the internal combustion engine and that exert a harmful influence on environment. More specifically, the exhaust gas concentration measuring part is not limited to a part that measures the concentration of CO, $CO_2$ and THC contained in the exhaust gas, and may be a part that also measures other component such as $NO_x$ contained in the exhaust gas simultaneously.

As mentioned above, in accordance with this invention, various effects can be produced such that the mass of the exhaust gas discharged from the internal combustion engine per unit output can be easily obtained without any time-lag by the use of the exhaust gas measuring device alone, the measurement can be conducted for any type of vehicles, and the measurement can be conducted while the vehicle is actually in motion on a real time basis.

DETAILED DESCRIPTION OF THE PREFERRED EMBODIMENTS

One embodiment of the present claimed invention will be described in detail with reference to FIG. 1 through FIG. 3.

Figure 1:
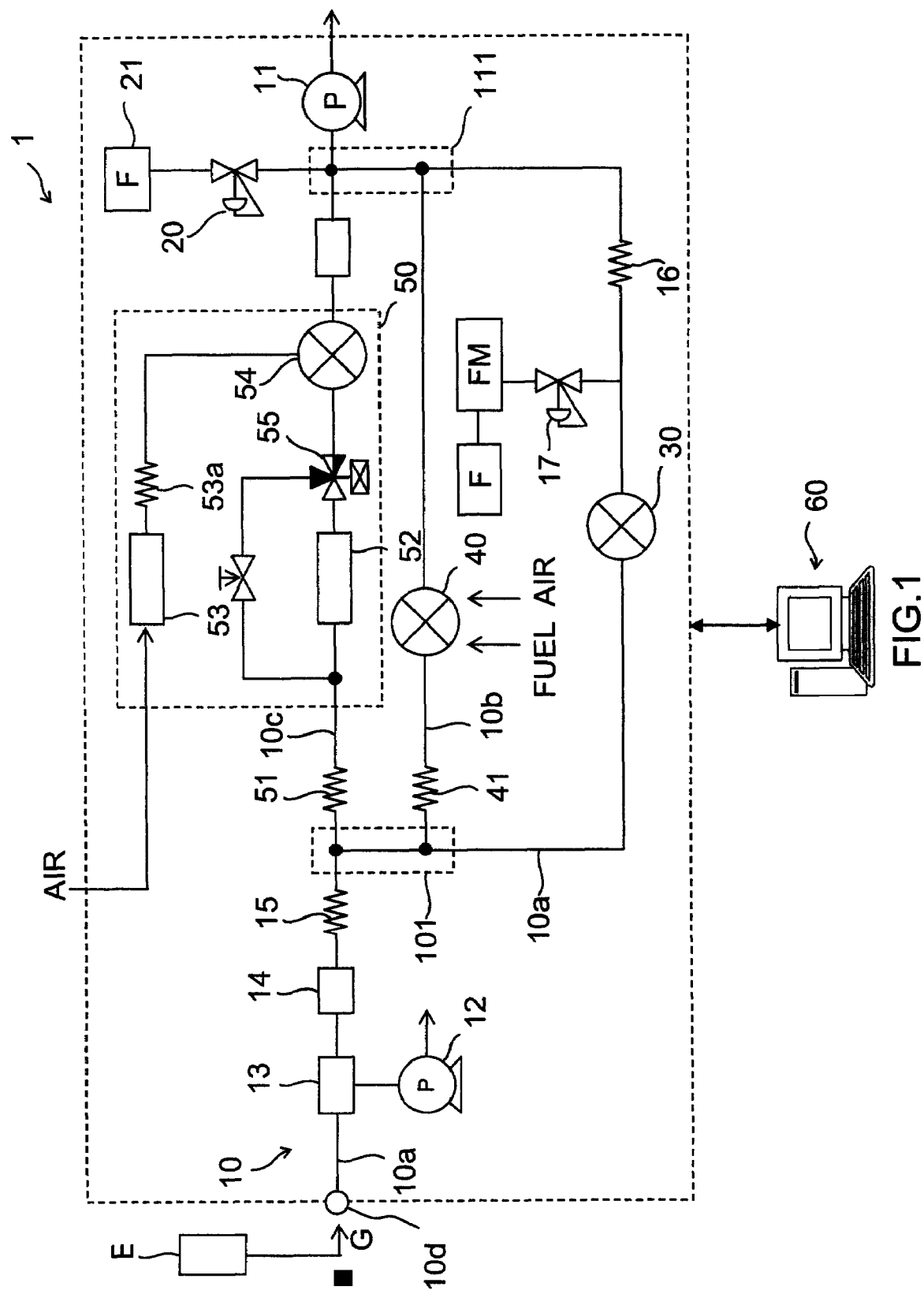
FIG. 1 is a schematic view showing a whole of an exhaust gas measuring device in accordance with a first embodiment of the present claimed invention.

An exhaust gas measuring device in accordance with this embodiment is of a vehicle-mountable type and the outline arrangement is shown in FIG. 1. The exhaust gas measuring device comprises a flow path system 10 into which exhaust gas G discharged from an internal combustion engine E of a vehicle such as an automobile is introduced, three analyzers 30, 40, 50, namely an infrared gas analyzer 30 that measures each concentration of CO, $CO_2$, and $H_2O$ in the exhaust gas G as being sample gas, a hydrogen flame ionization analyzer 40 that measures the concentration of THC (total hydrocarbon, hydrocarbon class), and a CLD type $NO_x$ analyzer 50 that measures the concentration of $NO_x$, and an information processing unit 60 that collects measured result data from each analyzer 30, 40, 50 and analyzes them in accordance with each object and that controls a pressure control valve arranged in the flow path system 10.

The flow path system 10 comprises a main flow path 10$a$ that plays a role as a bypath to pass almost all of the exhaust gas G discharged from the internal combustion engine E, and multiple (two) sub-flow paths 10$b$, 10$c$ arranged in parallel to the main flow path 10$a$. The infrared gas analyzer 30 is arranged on the main flow path 10$a$, the hydrogen flame ionization analyzer 40 and the CLD type $NO_x$ analyzer 50 are arranged on the sub-flow paths 10$b$ and 10$c$ respectively.

An upstream end of the main flow path 10$a$ opens as a main port 10$d$ and an exhaust duct of the vehicle is connected to the main port 10$d$ and an amount (a part or all) of the exhaust gas G discharged from the internal combustion engine E required for measurement is introduced into the main flow path 10$a$ by sucking the exhaust gas G by the use of a suction pump 11 arranged at the most downstream side of the main flow path 10$a$.

More concretely, in succession to the main port 10$a$ that introduces the exhaust gas G, a drain separator 13 that is connected to a pump 12 and that removes liquid moisture contained in the exhaust gas G, a filter 14, a flow rate control pipe (capillary) 15, a furcated part 101, the infrared gas analyzer 30, a flow rate control pipe (capillary) 16, an interflow part 111, the suction pump 11 are arranged serially in this order. A pressure control valve 17 is connected downstream of the infrared gas analyzer 30. The pressure control valve 17 controls the pressure in the flow path system between the capillary 14 and the capillary 16, and serves as a role to keep a flow rate and the pressure of the exhaust gas G flowing into the infrared gas analyzer 30 constant in cooperation with each capillary 14, 16.

The first and the second sub-flow paths 10b, 10c are so arranged to be furcated from the main flow path 10a at the furcated part 101 and to be connected to the main flow path 10a again at the interflow part 111.

The hydrogen flame ionization analyzer 40 that measures the concentration of THC in the exhaust gas G is arranged on the first sub-flow path 10b. A flow rate control pipe (capillary) 41 that flows an amount of the exhaust gas G necessary for measuring the concentration of THC into the hydrogen flame ionization analyzer 40 is arranged upstream of the hydrogen flame ionization analyzer 40. The amount of the exhaust gas G flowing into the first sub-flow path 10b is a very small amount compared with the amount of the exhaust gas G that flows into the main flow path 10a. In this embodiment, the amount of the exhaust gas G that flows into the main flow path 10a is set to be 2.5 L/min, while the amount of the exhaust gas G that flows into the first sub-flow path 10b is set to be 0.01 L/min.

A flow rate control pipe (capillary) 51 and the CLD type $NO_x$ analyzer 50 are arranged in this order from upstream on the second sub-flow path 10c. The flow rate control pipe (capillary) 51 is to limit an amount of the exhaust gas G that flows into the second sub-flow path 10c to a flow rate necessary for measuring the concentration of nitrogen oxide. The amount of the exhaust gas G flowing into the second sub-flow path 10c is a very small amount compared with the amount of the exhaust gas G that flows into the main flow path 10a. In this embodiment, the amount of the exhaust gas G that flows into the second sub-flow path 10c is set to be 0.07 L/min.

The pressure control valve 20 connected to the interflow part 111 communicates the interflow part 111 with open air through a filter 21 and controls the pressure in the sub-flow paths 10b, 10c, to be described later. More specifically, the pressure control valve 20 serves as a role to keep a flow rate and the pressure of the exhaust gas G flowing into the hydrogen flame ionization analyzer 40 and the CLD type $NO_x$ analyzer 50 constant in cooperation with each capillary 41, 51 arranged upstream of each sub-flow path 10b, 10c.

Next, each analyzer 30, 40, 50 will be generally explained.

The infrared gas analyzer 30 is to measure each amount (concentration) of CO, $CO_2$, and $H_2O$ by detecting absorbency that shows how much the infra-red ray of each characteristic wavelength is absorbed while the infra-red ray passes through the sample gas, since the infrared gas analyzer 30 is disposed to absorb the infra-red ray of the characteristic wavelength.

The hydrogen flame ionization analyzer 40 is of a type wherein fuel gas (hydrogen gas) is mixed into the exhaust gas G as being the sample gas at a constant ratio, the mixed gas is burned, a value of electric current generated due to ionization of THC (total hydrocarbons) contained in the sample gas is detected. The hydrogen flame ionization analyzer 40 can calculate an amount (concentration) of THC from the value of the electric current. In addition to the fuel gas, combustion supporting gas (air) also is introduced into the hydrogen flame ionization analyzer 40.

The CLD type $NO_x$ analyzer 50 can measure an amount (concentration) of $NO_x$ contained in the exhaust gas G and comprises, as shown in FIG. 1, an NO converter 52, an ozone generator 53, a photo detector (not shown in drawings), and a reactor 54. The NO converter 52 is to convert $NO_x$ into NO and arranged at one of a pair of the parallel paths that divide the introduced exhaust gas G that is introduced into the second sub-flow path 10c into two. An electromagnetic switch valve 55 is arranged at a terminal end of the parallel paths and the exhaust gas G is alternatively introduced into the reactor 54 only through either one of the parallel paths. The ozone generator 53 imports atmospheric air without dehumidification, converts oxygen contained in the atmospheric air into ozone and outputs it as ozone-containing gas through a capillary 53a. The reactor 54 is a box body having a certain cubic volume and comprises a sample gas introducing port, an ozone-containing gas introducing port and a leading-out port. The gas from either one of the parallel paths alternatively selected by the switch valve as above mentioned is introduced into the sample gas introducing port and the ozone-containing gas from the ozone generator 53 is introduced into the ozone-containing gas introducing port. Each gas is mixed inside the reactor 54, and light is emitted. The photo detector, not shown in drawings, is to measure the luminescence intensity in the reactor 54 and, for example, a photoelectron multiplier is used as the photo detector in this embodiment. In this embodiment, as mentioned above, since the CLD type $NO_x$ analyzer 50 is so arranged that the atmospheric air is introduced into the ozone generator 53 without dehumidification, it is possible to omit a dehumidifier and a drier that is necessary for a conventional analyzer. This arrangement makes it possible to reduce electrical consumption to a large extent and to downsize the analyzer, which makes this analyzer appropriate to be loaded on a vehicle.

The information processing unit 60 is to calculate the mass of each component contained in the exhaust gas G discharged from the internal combustion engine E per unit workload by providing a predetermined calculation to the measured data obtained from each analyzer 30, 40, 50 and the flow rate of the exhaust gas G discharged from the internal combustion engine E.

Figure 2:
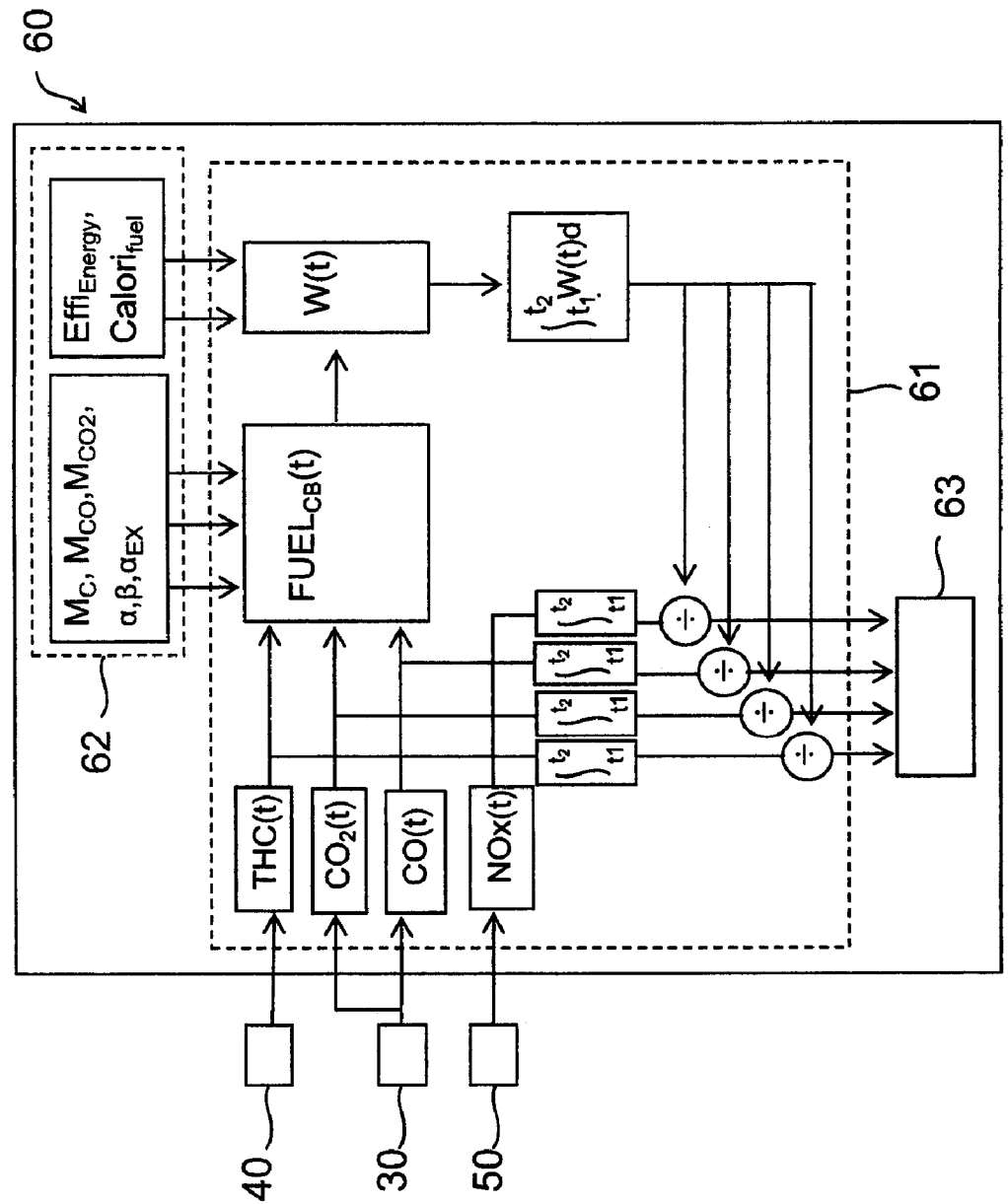
FIG. 2 is a block diagram showing an internal structure of an information processing unit included in the exhaust gas measuring device shown in FIG. 1.
Figure 3:
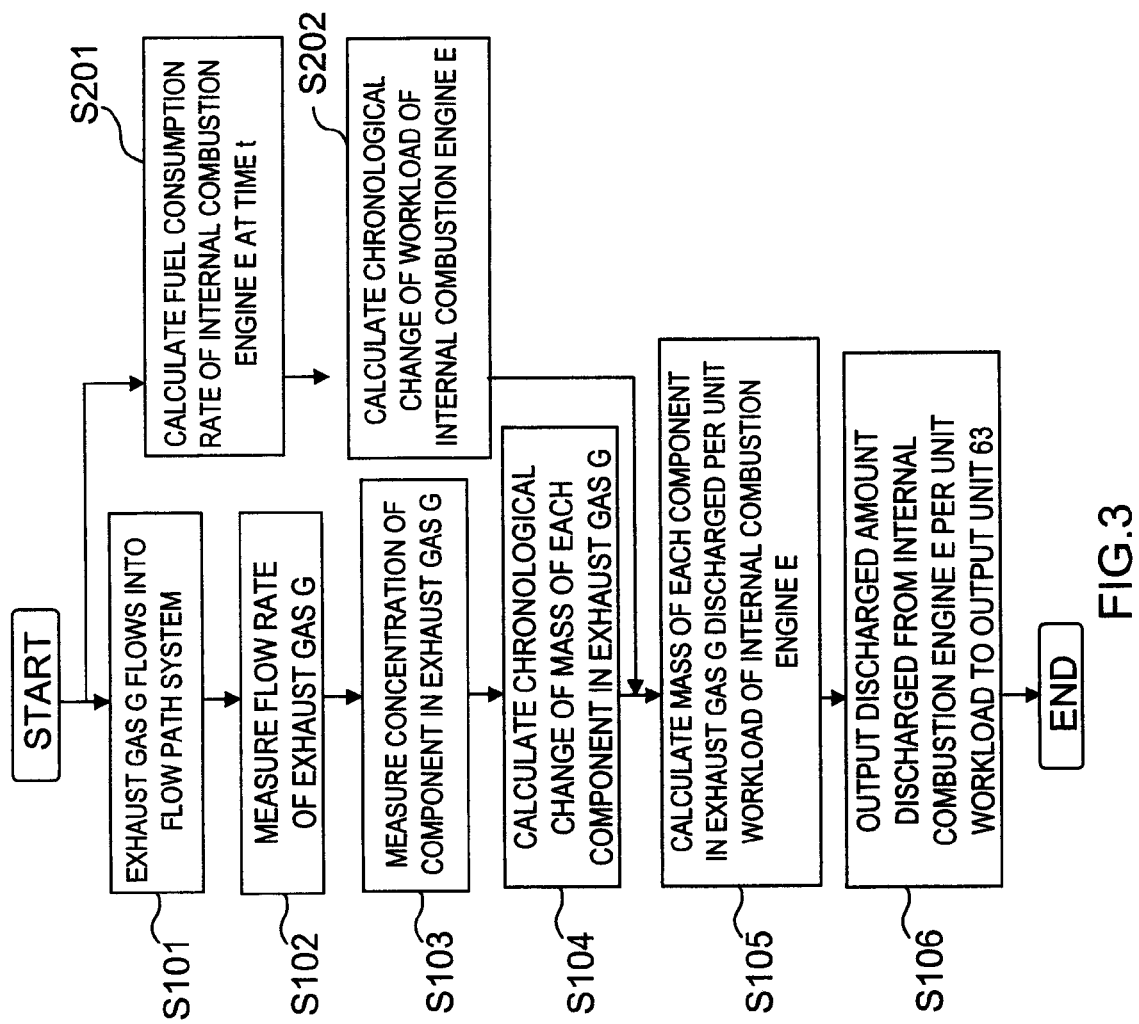
FIG. 3 is a flow chart showing a procedure to obtain the mass of each component in the exhaust gas discharged from an internal combustion engine per unit workload by the use of the exhaust gas measuring device shown in FIG. 1.

The information processing unit 60 comprises, as shown in FIG. 2, a computation part 61, a memory 62 to memorize predetermined data and an output device 63 such as a display to which a result calculated by the computation part 61 is output. In order to visually express what data is input or output, or what calculation is performed in the information processing unit 60 by giving an instruction signal from the computation part 61, a part of steps inside the information processing unit 60 is described in FIG. 2. The detailed steps will be explained by the use of the flow chart shown in FIG. 3.

Next, a general step of measuring the exhaust gas G discharged from the internal combustion engine E by each analyzer 30, 40, 50, calculating the mass of each component in the exhaust gas G discharged from the internal combustion engine E per unit workload and outputting them by the use of the exhaust gas measuring device 1 in accordance with this embodiment will be explained with reference to FIG. 3. In this embodiment, an example of a case of obtaining a time-series change of workload of the internal combustion engine E and a time-series change of the mass of each component contained in the exhaust gas G discharged from the internal combustion engine E during an appropriate time zone from $t_1$ to $t_2$ and obtaining an average mass of each component per unit workload during this time zone will be shown.

First, the exhaust gas G discharged from the internal combustion engine E flows into the flow path system 10 through the main port 10d. The exhaust gas G flowing into the flow path system 10 is furcated at the furcated part 101 and each furcated exhaust gas G flows into the main flow path 10a, the first sub-flow path 10b and the second sub-flow path 10c respectively (S101).

At this time a total flow rate of the exhaust gas G discharged from an exhaust duct of the internal combustion engine E is measured in a time-series order by a flow rate measuring device (not shown in drawings) such as an arbitrarily arranged flow meter and the measured time-series change is sequentially transmitted to the computation part 61 of the information processing device 60 (S102).

The concentration of the predetermined component in the exhaust gas G flowing into each flow path 10a, 10b, 10c is measured in a time-series order by each analyzer 30, 40, 50, and the measured value of the concentration is transmitted to the computation part 61 (S103). More specifically, the concentration of each component of CO, $CO_2$ and THC is measured in a time-series order by the infra-red gas analyzer 30 and the hydrogen flame ionization analyzer 40 and the amount (concentration) of $NO_x$ contained in the exhaust gas G is measured in a time-series order by the CLD type $NO_x$ analyzer 50. The computation part 61 first corrects the measured value so as to obtain the concentration of the exhaust gas G at an identical time in consideration of time deviance of the exhaust gas G flowing into each analyzer 30, 40, 50.

Next, the computation part 61 integrates the total flow rate of the exhaust gas G and the concentration of the component and calculates a time-series change of the mass of each component contained in the exhaust gas G discharged from the internal combustion engine E (S104). The time-series change of the mass of each component is expressed as an instant discharged amount of each component at the time t as follows.

Instant discharged amount of CO at time t [g/s]:
$CO_{MASS}(t)$ [g/s]

Instant discharged amount of $CO_2$ at time t [g/s]:
$CO_{2MASS}(t)$ [g/s]

Instant discharged amount of THC at time t [g/s]:
$THC_{MASS}(t)$ [g/s]

Next, the computation part 61 obtains a fuel consumption rate $Fuel_{CB}(t)$ of the internal combustion engine E at the time t by substituting the instant discharged amount of CO, $CO_2$ and THC at the time t calculated in the step S103 ($CO_{MASS}(t)$ [g/s], $CO_{2MASS}(t)$ [g/s], $THC_{MASS}(t)$ [g/s]) into the arithmetic equation shown as (equation 1)(S201). In the equation 1, $R_{CWFHC}$ expresses an average carbon mass rate of HC in the exhaust gas G, $R_{CWF}$ expresses a carbon mass rate of the fuel, and $R_{CWFHC}$ and $R_{CWF}$ can be obtained by the use of an atomic mass of carbon Mc (=12), a molecular mass of carbon monoxide Mco (=28), a molecular mass of carbon dioxide $Mco_2$ (=44), a ratio of number of atoms between hydrogen and carbon of the fuel α (=1.85), a ratio of number of atoms between oxygen and carbon of the fuel β (=0.00), and an average ratio of number of atoms between hydrogen and carbon of HC in the exhaust gas G $α_{EX}$ (=1.85).

$$Fuel_{CB}(t) = \frac{R_{CWFHC} \times HC_{MASS}(t) + \frac{Mc}{Mco} \times CO_{MASS}(t) + \frac{Mc}{Mco_2} \times CO_{2MASS}(t)}{R_{CWF}} \quad \text{(Equation 1)}$$

$$R_{CWF} = \frac{Mc}{\alpha \times M_H + \beta \times Mo + Mc} \quad \text{(Equation 2)}$$

$$R_{CWFHC} = \frac{Mc}{\alpha_{EX} \times M_H + Mc} \quad \text{(Equation 3)}$$

Then the time-series change of the workload Work(t) [kW] of the internal combustion engine E is calculated from the combustion efficiency $Effi_{Energy}$ of the internal combustion engine E that has been previously memorized in the memory 62 and the fuel consumption rate $Fuel_{CB}(t)$ of the internal combustion engine E obtained in S201 (S202). An equation to calculate the time-series change of the workload of the internal combustion engine E Work(t) is shown in equation 4. In the equation 4, $Calori_{fuel}$ [kJ/g] expresses known combustion energy [kJ/kg] per unit mass of the fuel combusted by the internal combustion engine E.

$$Work(t)\_kW = Calori_{fuel} \times Fuel_{CB(t)} \times \frac{1}{1000} \times Effi_{Energy} \times \frac{1}{100} \quad \text{(Equation 4)}$$

The mass of each component in the exhaust gas G discharged from the internal combustion engine E per unit workload is calculated by dividing the mass (the instant discharged amount) $CO_{MASS}(t)$ [g/s], $CO_{2MASS}(t)$ [g/s], $THC_{MASS}(t)$ [g/s] of each component contained in the exhaust gas G at the time t obtained in the step S104 by the time-series change Work(t) of the workload of the internal combustion engine E obtained in the step S202 (S105).

More concretely, in case of calculating the mass of CO in the exhaust gas G discharged from the internal combustion engine E per unit workload during a time, for example, from the time t1 to the time t2, the workload $W_{t1-t2}$ [kW] of the internal combustion engine E during the time from t1 to t2 is calculated from a conversion equation shown in the equation 5, the CO discharged amount $CO_{MASS\_t1-t2}$ [g] during the time t1 to t2 is calculated from a conversion equation shown in the equation 6 and then $CO_{MASS\_t1-t2}$ is divided by $W_{t1-t2}$. This makes it possible to obtain the CO discharged amount (mass) discharged from the internal combustion engine E per unit workload during the time from $t_1$ to $t_2$.

$$W_{t1-t2} = \sum_{t1}^{t2} Work(t) \times \frac{1}{3600} \quad \text{(Equation 5)}$$

$$CO_{MASS\_t1-t2} = \sum_{t1}^{t2} CO_{MASS}(t) \quad \text{(Equation 6)}$$

Then data concerning the discharged amount (the mass) discharged from the internal combustion engine E per unit workload for each component in the exhaust gas G is output to the output unit 63 (S106).

Figure 4:
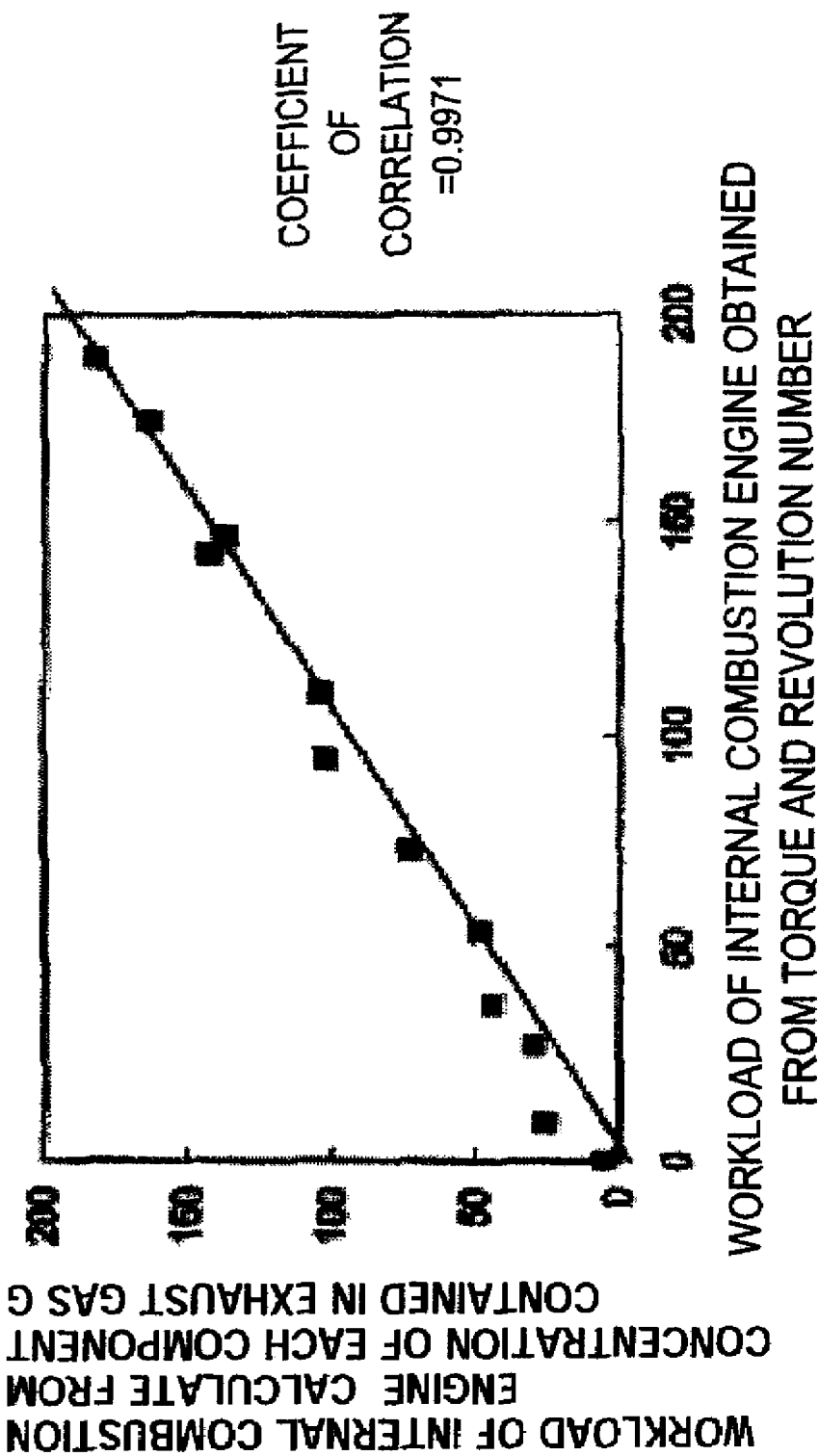
FIG. 4 is a graph showing a correlation between the workload obtained from the torque and the rotation number of the internal combustion engine and the workload of the internal combustion engine obtained as a result of obtaining the fuel consumption rate of the internal combustion engine by the use of each concentration of CO, $CO_2$ and THC.

It is confirmed by an experiment that thus obtained workload generally matches a workload calculated from measured data of torque and a rotation number of the internal combustion engine E. The graph shown in FIG. 4 expresses the workload of the internal combustion engine E obtained from the torque and the number of rotations on the x-axis and the workload of the internal combustion engine E obtained from the result of the fuel consumption rate $Fuel_{CB}$ of the internal combustion engine E by the use of the concentration of CO, $CO_2$, and THC contained in the exhaust gas G on the y-axis. As is clear from this graph, the workload of the internal combustion engine E obtained in the above-mentioned embodiment is in an extremely high correlation (correlation coefficient=0.9971) with the measured workload of the internal combustion engine E, which shows that the workload of the internal combustion engine E obtained in the embodiment is a value measured accurately.

As a result, in accordance with this invention, since the workload of the internal combustion engine is calculated from the combustion efficiency of the internal combustion engine and the fuel consumption rate of the internal combustion engine, it is possible to calculate the mass of each component in the exhaust gas discharged from the internal combustion engine per unit workload easily without using the torque data of the ECU.

In addition, since there is no need of using the data from the ECU, measurement can be conducted also in a state that the internal combustion engine is separated from a vehicle, in addition to the case that the measurement is conducted for the internal combustion engine (an engine) loaded on a vehicle. As a result, in spite of a case that it is unable to measure the exhaust gas discharged from an engine of a vehicle while the vehicle is in motion with the exhaust gas measuring device loaded on a chassis dynamo because a size of the vehicle itself is extremely big like a large-size diesel vehicle, the mass of each component in the exhaust gas discharged from a diesel engine per unit workload can be calculated after dismounting the diesel engine alone and the mass can be measured easily also while a vehicle is in motion with the diesel engine loaded on the vehicle.

The present claimed invention is not limited to the above-mentioned embodiment.

For example, in case of obtaining the mass of each component in the exhaust gas of the internal combustion engine per unit workload more efficiently in response, the time zone from $t_1$ to $t_2$ may preferably be set to be an extremely short period (for example, 0.5 second). In this case, the mass of each component discharged from the internal combustion engine of the moving vehicle per unit workload can be obtained on a real time basis.

In addition, the time zone from $t_1$ to $t_2$ may be set to correspond to a period from a starting time to an ending time of one stroke of a piston cylinder of the internal combustion engine and data concerning the discharged amount (mass) discharged from the internal combustion engine E per unit workload may be continuously obtained during this time zone from $t_1$ to $t_2$ $(=\Delta t)$. In this case, since the mass of each component in the exhaust gas discharged from the internal combustion engine E and the workload of the internal combustion engine E can be obtained respectively for each stroke that the internal combustion engine E pulsates, it is possible to obtain the data effective for checking performance or characteristics of the internal combustion engine in detail.

There may be various modifications without departing from the spirit of the invention.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

The invention claimed is:

1. An exhaust gas measuring device comprising:
an exhaust gas concentration measuring part that measures concentration of a component related to a carbon compound in exhaust gas discharged from an internal combustion engine;
wherein a discharged amount of the component related to the carbon compound is calculated based on the measured concentration of the component related to the carbon compound and a flow rate of the exhaust gas, and a workload of the internal combustion engine is calculated based on the discharged amount; and
wherein the component related to the carbon compound is a plurality of components including at least CO, $CO_2$ and a hydrocarbon class.

2. The exhaust gas measuring device of claim 1, wherein mass of the exhaust gas discharged from the internal combustion engine per unit workload is calculated based on the workload of the internal combustion engine.

3. The exhaust gas measuring device of claim 1, wherein mass of a predetermined component in the exhaust gas discharged from the internal combustion engine per unit workload is calculated based on the workload of the internal combustion engine.

4. The exhaust gas measuring device of claim 1, wherein an amount of fuel consumption is calculated based on the discharged amount of the component related to the carbon compound and the workload of the internal combustion engine is calculated by multiplying predetermined combustion energy of the fuel by a combustion efficiency of the internal combustion engine.

5. The exhaust gas measuring device of claim 1, wherein the concentration of the compound related to the carbon compound in the exhaust gas is obtained by integration in a particular time zone and a discharged amount of the component related to the carbon compound in the exhaust gas discharged from the internal combustion engine in the time zone is calculated based on the integrated value of the concentration.

6. The exhaust gas measuring device of claim 5, wherein the time zone is determined in accordance with a pulsation cycle of flow of the exhaust gas.

7. The exhaust gas measuring device of claim 5, wherein mass of the exhaust gas discharged from the internal combustion engine per unit workload is calculated based on the workload of the internal combustion engine.

8. The exhaust gas measuring device of claim 5, wherein mass of a predetermined component in the exhaust gas discharged from the internal combustion engine per unit workload is calculated based on the workload of the internal combustion engine.

9. The exhaust gas measuring device of claim 5, wherein an amount of fuel consumption is calculated based on the discharged amount of the component related to the carbon compound and the workload of the internal combustion engine is calculated by multiplying predetermined combustion energy of the fuel by a combustion efficiency of the internal combustion engine.

* * * * *